(12) United States Patent
Beer et al.

(10) Patent No.: US 9,409,177 B2
(45) Date of Patent: Aug. 9, 2016

(54) CHIP-BASED DEVICE FOR PARALLEL SORTING, AMPLIFICATION, DETECTION, AND IDENTIFICATION OF NUCLEIC ACID SUBSEQUENCES

(75) Inventors: Neil Reginald Beer, Pleasanton, CA (US); Billy W. Colston, Jr., San Ramon, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 1341 days.

(21) Appl. No.: 12/401,714

(22) Filed: Mar. 11, 2009

(65) Prior Publication Data

US 2010/0015614 A1 Jan. 21, 2010

Related U.S. Application Data

(60) Provisional application No. 61/038,495, filed on Mar. 21, 2008.

(51) Int. Cl.
*C12Q 1/68* (2006.01)
*C12M 1/34* (2006.01)
*B01L 7/00* (2006.01)
*B01L 3/00* (2006.01)

(52) U.S. Cl.
CPC ........... *B01L 7/525* (2013.01); *B01L 3/502792* (2013.01); *B01L 3/502761* (2013.01); *B01L 2200/0652* (2013.01); *B01L 2300/087* (2013.01); *B01L 2300/0864* (2013.01); *B01L 2300/0867* (2013.01); *B01L 2300/1822* (2013.01); *B01L 2300/1827* (2013.01); *B01L 2400/0415* (2013.01); *B01L 2400/0421* (2013.01); *B01L 2400/0454* (2013.01); *C12Q 1/686* (2013.01)

(58) Field of Classification Search
None
See application file for complete search history.

(56) References Cited

U.S. PATENT DOCUMENTS

| 2002/0090649 | A1* | 7/2002 | Chan et al. | 435/7.1 |
|---|---|---|---|---|
| 2004/0086869 | A1* | 5/2004 | Schembri | 435/6 |
| 2004/0101445 | A1* | 5/2004 | Shvets et al. | 422/100 |
| 2008/0003142 | A1* | 1/2008 | Link et al. | 422/82.08 |
| 2008/0044893 | A1* | 2/2008 | Pollack et al. | 435/305.3 |
| 2008/0166793 | A1 | 7/2008 | Beer et al. | |

FOREIGN PATENT DOCUMENTS

WO   WO 2007/124346 A2   11/2007

OTHER PUBLICATIONS

Vijay Srinivasan, et al "An integrated digital microfluidic lab-on-a-chip for clinical diagnostics on human physiologic fluids", Lab Chip, 2004, 4, 310-315.
Aaron R. Wheeler, et al, Digital Microfluidics with In-Line Sample Purification for Proteomics Analyses with MALDI-MS, Analytical Chemistry, vol. 77, No. 2, Jan. 15, 2005. 534-540.
Jon A Schwartz, et al, Droplet-based chemistry on a programmable micro-chip, Lab Chip, 2004, 4, 11-17.
Peter R. C. Gascoyne, et al, Dielectrophoresis-based programmable fluidic processors, Lab Chip, 2004, 4, 299-309.

* cited by examiner

*Primary Examiner* — David Thomas
(74) *Attorney, Agent, or Firm* — Eddie E. Scott

(57) ABSTRACT

An apparatus for chip-based sorting, amplification, detection, and identification of a sample having a planar substrate. The planar substrate is divided into cells. The cells are arranged on the planar substrate in rows and columns. Electrodes are located in the cells. A micro-reactor maker produces micro-reactors containing the sample. The micro-reactor maker is positioned to deliver the micro-reactors to the planar substrate. A microprocessor is connected to the electrodes for manipulating the micro-reactors on the planar substrate. A detector is positioned to interrogate the sample contained in the micro-reactors.

10 Claims, 6 Drawing Sheets

CHIP-BASED DEVICE FOR PARALLEL SORTING, AMPLIFICATION, DETECTION, AND IDENTIFICATION OF NUCLEIC ACID SUBSEQUENCES

CROSS-REFERENCE TO RELATED APPLICATIONS

The present application claims benefit under 35 U.S.C. §119(e) of U.S. Provisional Patent Application No. 61/038,495 filed Mar. 21, 2008 entitled "Chip-based device for parallel sorting, amplification, detection, and identification of nucleic acid subsequences in a complex mixture," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA2.7344 between the United States Department of Energy and Lawrence Livermore National Security, LLC for the operation of Lawrence Livermore National Laboratory.

BACKGROUND

1. Field of Endeavor

The present invention relates to microfluidics and more particularly to a system, for performing parallel nucleic acid sorting, amplification and characterization.

2. State of Technology

There are an estimated $10^{31}$ viruses on Earth, making them by far the most abundant biological entities, Identifying and measuring viruses in clinical or environmental sample is extremely challenging. Many viruses are impossible to culture, making traditional phenotypic characterization infeasible. Viruses, compared to micro-organisms and higher life forms, evolve rapidly (particularly RNA viruses) making large fractions of the genome susceptible to genetic drift and shift. It is not unusual for two descendent viruses that produce similar disease to have multiple mutations across the genomes. With no gene fidelity, profiling (including detection) cannot be accomplished using conserved sequences. Some insight into this problem has been gained through viral metagenomics. Viral metagenomics is a rapidly emerging field that has produced relatively small numbers of publications. There are, to the best of our knowledge, six published viral metagenomic libraries. Only one of these studies included RNA viruses. Samples were collected from human faeces, marine sediment, and seawater. Over 65% of metagenomic sequences had no homologues in the non-redundant databases, a tribute to the paucity of diversity in our current GenBank database and limitations of the current search algorithms. We are currently ill-prepared to deal with novel pathogens (natural or engineered), complex mixtures of organisms, or detection of virulence regardless of the organism conferring it. This problem is compounded by our near-total lack of knowledge of "normal" viral backgrounds in environmental, human, and agricultural samples.

The present invention provides a system for taking a complex sample and isolating individual single or double stranded nucleic acids within their own subnanoliter size reactors, amplifying the target nucleic acid through PCR, sorting out nucleic acid from non-nucleic acid reactors, and characterizing the selected nucleic acid reactors through capillary electrophoresis. The present invention also allows the detection and characterization of novel viruses and organisms by allowing the sequencing of previously unknown genetic material. The present invention allows for: reduction of costly reagent volumes, production of massively parallel and inexpensive microfluidic analysis chips, and scalable mass production of such chips. Technologies that could compete with the present invention are mainly robotic-based systems. These devices typically couple auto-pipettes with robotic manipulators to measure, mix, and deliver sample and reagents. These devices are relatively complex, expensive, and difficult to miniaturize.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for performing nucleic acid sorting, amplification, and characterization by microdroplet polymerase chain reaction amplification followed by characterization such as capillary electrophoresis analysis and potential genomic sequencing, all performed on an integrated coplanar microfluidic system. The present invention provides an apparatus for chip-based sorting, amplification, detection, and identification of a sample having a planar substrate. The planar substrate is divided into cells. The cells are arranged on the planar substrate in rows and columns. Electrodes are located in the cells. A microreactor maker produces micro-reactors containing the sample. The micro-reactor maker is positioned to deliver the micro-reactors to the planar substrate. A microprocessor is connected to the electrodes for manipulating the micro-reactors on the planar substrate. A detector is positioned to interrogate the sample contained, in the micro-reactors.

In various embodiments, the present invention provides a method for performing planar mixing, reaction, delivery, amplification, detection, and archival of target nucleic acid sample(s) and reagent(s). In addition, an embodiment of the invention describes a method for decontaminating the system during sample injection, mixing, amplification, and detection steps, allowing for continuous operation.

The present invention has uses in biowarfare detection applications for identifying, detecting, and monitoring bio-threat agents that contain nucleic acid signatures, such as spores, bacteria, viruses etc. The present invention has uses in biomedical applications for tracking, identifying, and monitoring outbreaks of infectious disease including emerging, previously unidentified and genetically engineered pathogens and for automated processing, amplification, and detection of host or microbial and viral DNA or RNA in biological fluids for medical purposes. The present invention has uses in forensic applications for automated processing, amplification, and detection DNA in biological fluids for forensic purposes. The present invention has uses in food and beverage safety for automated food testing for bacterial or viral contamination and for high throughput genetic screening for drug discovery and novel therapeutics.

In one embodiment the present invention includes an apparatus for chip-based sorting, amplification, defection, and identification of a sample having a planar substrate, the planar substrate divided into cells; the cells arranged on the planar substrate in rows and columns; electrodes in the cells; a micro-reactor maker for producing micro-reactors containing the sample, the micro-reactor maker positioned to deliver the micro-reactors to the planar substrate; a microprocessor connected to the electrodes for manipulating the micro-reactors on the planar substrate, and a detector positioned to interrogate the sample contained in the micro-reactors. Another embodiment of the present invention provides a method of chip-based sorting, amplification, detection, and identification of a sample including the steps of providing a planar substrate; dividing the planar substrate into cells, arranging the cells on the planar substrate in rows and columns; positioning electrodes in the cells; using a micro-reactor maker for producing micro-reactors containing the sample and delivering the micro-reactors to the cells on the planar substrate; connecting a microprocessor to the electrodes; using the microprocessor for manipulating the micro-reactors on the planar substrate, and using a detector to interrogate the sample contained in the micro-reactors.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Figure 1:
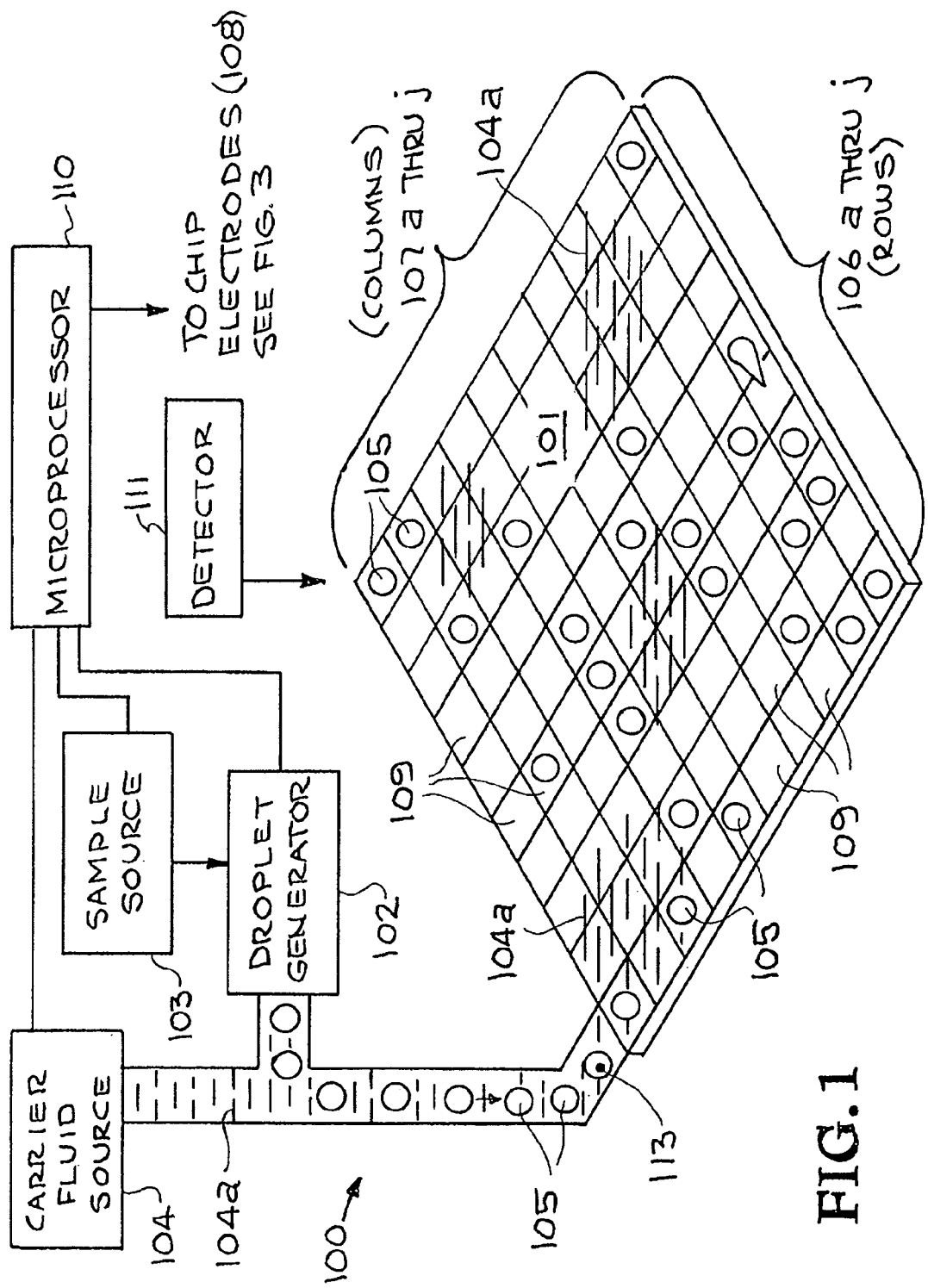
FIG. 1 illustrates one specific embodiment of a system incorporating the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Specific Embodiment—System 100

Referring now to the drawings and in particular to FIG. 1, one specific embodiment of a system incorporating the present invention will be described. The system is designated generally by the reference numeral 100. The system 100 includes the following structural elements: planar substrate 101, droplet generator 102, sample 103, carrier fluid 104, droplets (micro-reactors) 105, rows 106a through 106J, columns 107a through 107J, electrodes 108, barcode or radio identification tag 113, microprocessor 110, and detector 111.

The planar substrate 101 contains one hundred cells 109, however it is to be understood that other embodiments contain other numbers of cells, both more than one hundred and less than one hundred. The one hundred cells are identified by ten rows 106a through 106j and ten columns 107a through 107j. The droplet generator 102 produces individual droplets or micro-reactors 105 containing bacteria, viruses, viral particles, proteins, nucleic acids, or other matter which are introduced to the planar substrate 101 and will be manipulated on the planar substrate 101 as will hereinafter be described. The detector 111 provides detection specific droplets positioned in specific cells.

The droplet generator 102 and the detector 111 can be a droplet generator and detector as described in U.S. Published Patent Application No. 2008/0166793 by Nell R. Beer et al for sorting, amplification, detection, and identification, published Jul. 10, 2008 which is incorporated herein in its entirety by this reference. Manipulation of the micro-reactors 105 on the planar substrate 101 can be as described in the following articles which are incorporated herein in their entirety by this reference: "Digital Microfluidics with In-Line Sample Purification for Proteomics Analyses with MALDI-MS," by Aaron R. Wheeler et al, Anal. Chem. 2005, 77, 534-540; "An Integrated digital microfiuidic lab-on-a-chip for clinical diagnostics on human physiological fluids," by Vijay Srinivasan et al, in Miniaturisation for Chemistry, Biology & Bioengineering, First published as an Advance Article on the web 26 May 2004; "Droplet-based chemistry on a programmable microchip," by Jon A. Schwartz, et al, in Miniaturisation for Chemistry, Biology & Bioengineering, First published as an Advance Article on the web 26th Nov. 11, 2003; "Principles of droplet electrohydrodynamics for lab-on-a-chip," in Miniaturisation for Chemistry, Biology & Bioengineering, First published as an Advance Article on the web 26th Jul. 1, 2004; and "Dielectrophoresis-based programmable fluidic processors," by Peter R, C. Gaseoyne in Miniaturisation for Chemistry, Biology & Bioengineering, First published as an Advance Article on the web 26th Jul. 1, 2004.

The planar substrate 101 is washed in a continuous flow of oil which protects the substrate 101 from chemical contamination. Aqueous droplets or micro-reactors 105 containing bacteria, viruses, viral particles, proteins, nucleic acids, or other matter are introduced down the first column 106. As the micro-reactors 105 flow down the column 106 under diectrophoretic transfer, a microprocessor 110 monitoring the substrate recognizes available open rows. The microprocessor 110 then commands the electrodes 108 between two adjacent columns 107 to fire, diverting a downward moving micro-reactors 105 onto the adjacent column 1-7 to the right. This micro-reactors 105 is then mixed with reagent droplets in the next column or columns 107, which themselves were moved down their columns in similar fashion. The microreactor 105 can interrogated by detector 111. In this way different microreactor 105 can receive different reagents, allowing for sequential testing and detection using optical probes. A highly focused laser or chemical agent may then be employed to lyse the viral coat or bacterial wall within the microreactor 105. Specific individual micro-reactors 105 can be monitored using a barcode or radio identification tag 113. For example, International Patent Publication No. WO/2007/124346 by Archivex LLC published Nov. 1, 2007 describes liquid cartridges uniquely labeled by human-readable label, barcode label, and/or RFID (Radio Frequency Identification) tag and linked to database systems used for tracking and linking samples to specific experiments and dispensing jobs. International Patent Publication No. WO/2007/124346 is incorporated herein by this reference.

Specific Embodiment—System 200

Figure 2:
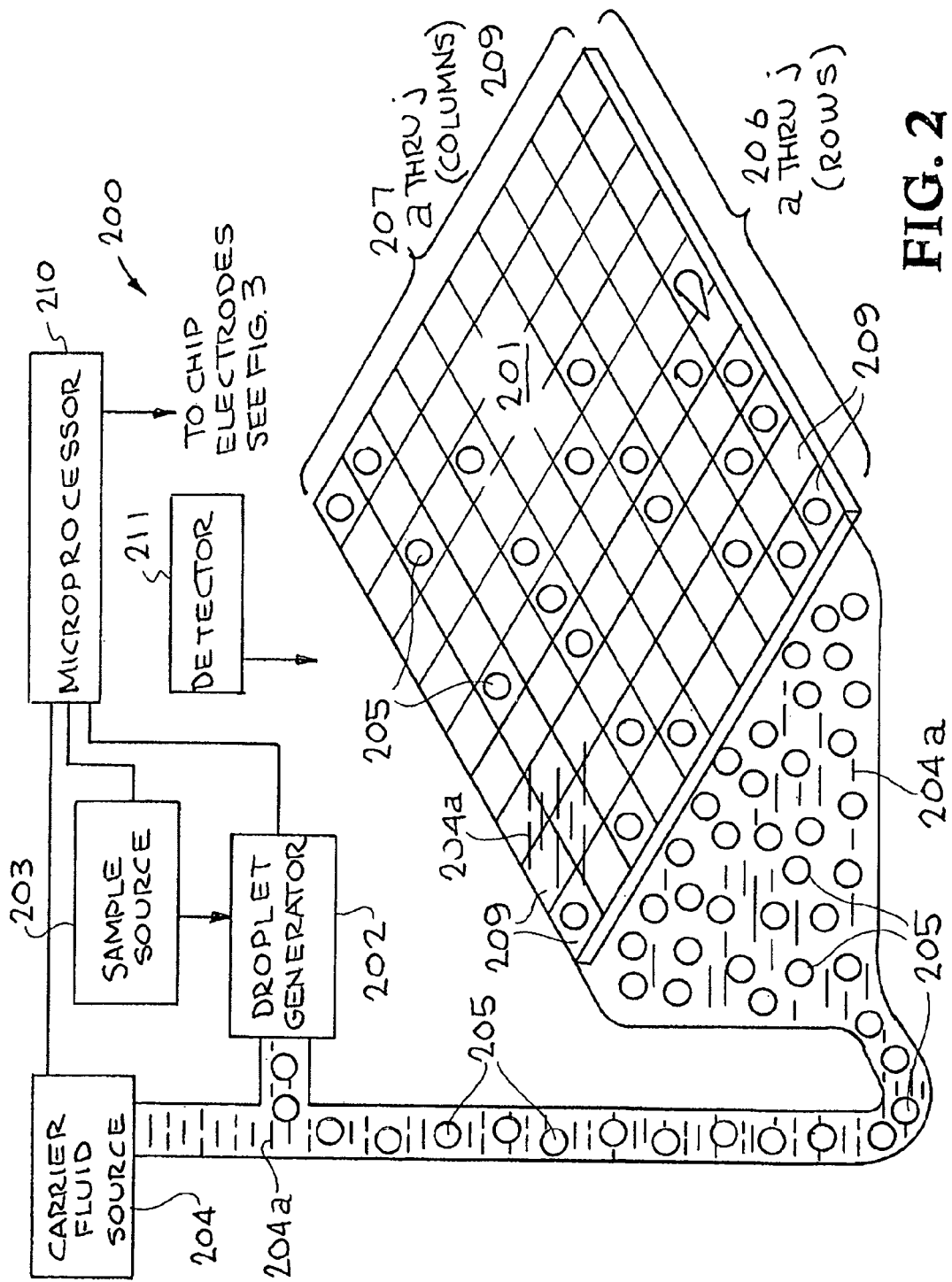
FIG. 2 illustrates another embodiment of a system incorporating the present invention.

Referring now to FIG. 2, another embodiment of a system incorporating the present invention will be described. The system is designated generally by the reference numeral 200. The system 200 includes the following structural elements: planar substrate 201, droplet generator 202, sample 203, carrier fluid 204, droplets (micro-reactors) 205, rows 206a-j, columns 207a-j, electrodes 208, cells 209, microprocessor 210, and detector 211. The planar substrate 201 contains one hundred cells. The one hundred cells are identified by ten rows 206a through 206j and ten columns 207a through 207j. The droplet generator 202 produces individual droplets or micro-reactors 205 containing bacteria, viruses, viral particles, proteins, nucleic acids, or other matter which are introduced to the planar substrate 201 and will be manipulated on the planar substrate 201 as will hereinafter be described. The detector 211 provides detection of individual droplets positioned in an individual cell.

The planar substrate 201 is washed in a continuous flow of oil which protects the substrate 201 from chemical contamination. Aqueous droplets or micro-reactors 205 containing bacteria, viruses, viral particles, proteins, nucleic acids, or other matter are introduced down the first column 206. As the micro-reactors 205 flow down the column 206 under diectrophoretic transfer, a microprocessor 210 monitoring the substrate recognizes available open rows. The microprocessor 210 then commands the electrodes 208 between two adjacent columns 207 to fire, diverting a downward moving microreactor 205 onto the adjacent column 1-7 to the right. This microreactor 205 is then mixed with reagent droplets in the next column or columns 207, which themselves were moved down their columns in similar fashion. The microreactor 205 can interrogated by detector 211. In this way different microreactor 205s can receive different reagents, allowing for sequential testing and detection using optical probes. A highly focused laser or chemical agent may then be employed to lyse the viral coat or bacterial wall within the microreactor 205.

Figure 3:
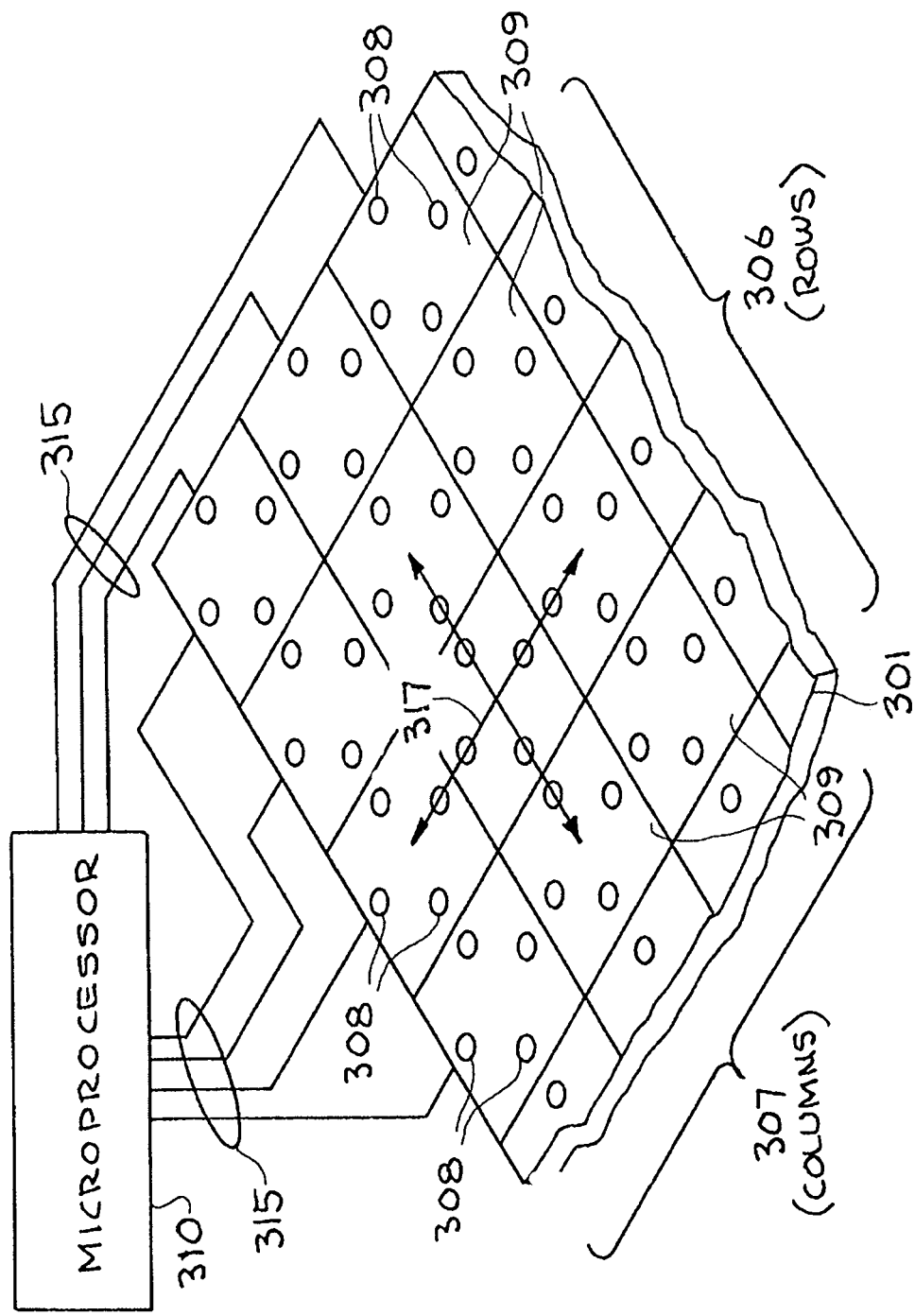
FIG. 3 provides additional details of the microprocessor of FIGS. 1 and 2.

Referring now to FIG. 3, the microprocessor 310 and its relation to the system will be described. The system contains the basic structural elements of the embodiments shown in FIGS. 1 and 2 with additional description of the microprocessor 310 provided. The sample loading unit introduces the micro-reactors into rows 306. The micro-reactors can be moved in columns 307 using the electrodes 308 to provide a voltage differential that moves the micro-reactors from one cell to another in columns 307.

Specific Embodiment—System 400

Figure 4:
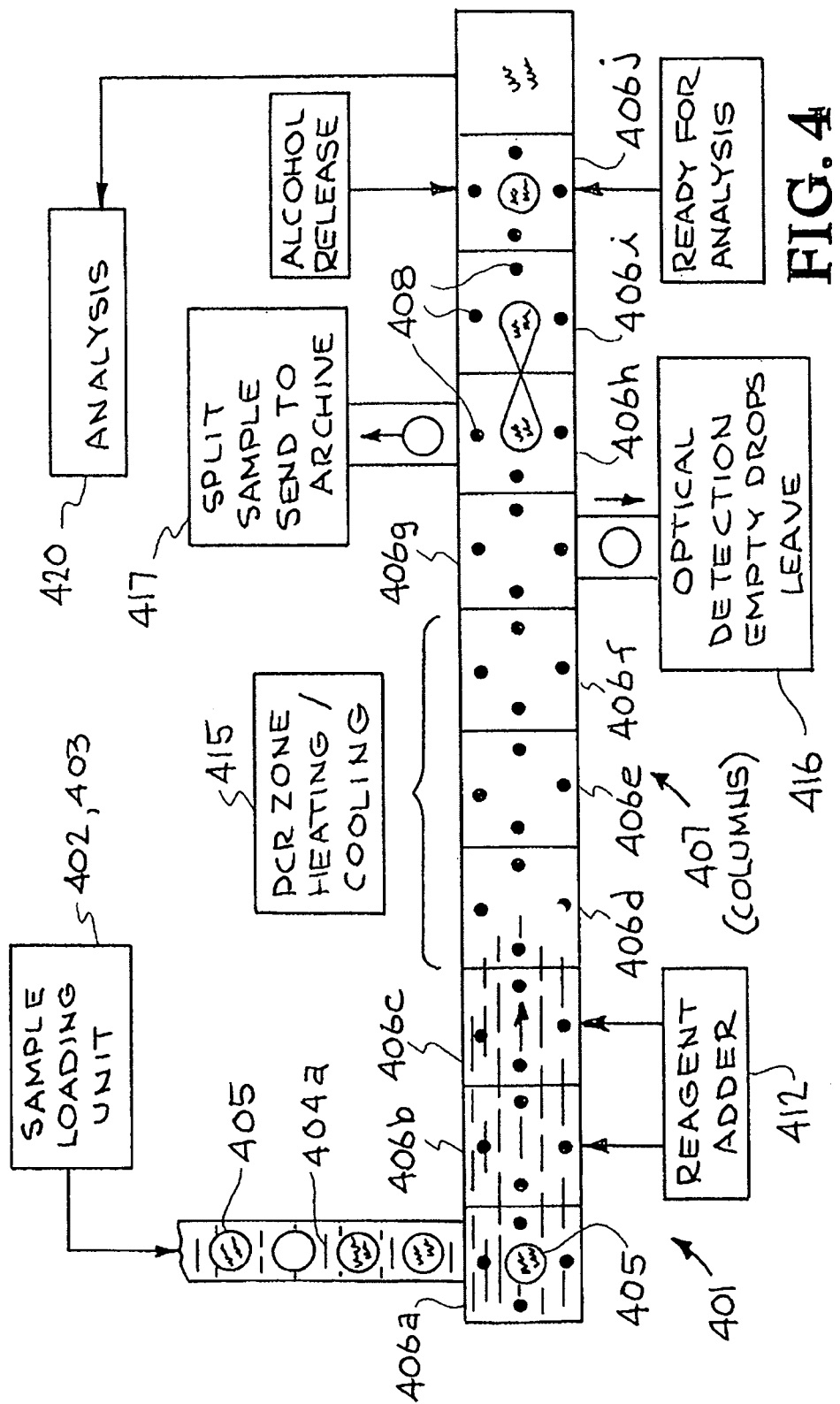
FIG. 4 illustrates an embodiment of a system that includes PCR heating and cooling.

Referring now to FIG. 4, another embodiment of a system incorporating the present invention will be described that includes PCR heating and cooling. FIG. shows a single column of the overall system and the system is designated generally by the reference numeral 400. The system 400 contains the basic structural elements of the embodiments shown in FIGS. 1, 2, and 3. The elements of the system 400 show in FIG. 4 used to describe the PCR heating and cooling include a planar substrate or chip 401, a sample loading unit 402 that can include a droplet generator, a sample 403 carried by a carrier fluid 404a, droplets or micro-reactors 405, rows 406a-j, columns 407a-j, electrodes 408, PCR zone 415, optical detection, zone 416, and archive 417.

The sample loading unit 402 introduces the micro-reactors 405 into row 406a. The micro-reactors 405 can be moved in columns using the electrodes 408 to provide a voltage differential that moves the micro-reactors 405 from one cell to another in columns. The reagents adder 412 in the rows allows the adding of reagents for further processing.

The droplets, each of which provide an isolated mobile PCR reactor 405 containing lysed-particle analyte plus reagent and buffer mixture, moves into PCR rows of the PCR zone 415. The micro-reactors 405 are cycled from heating cells in row 406b to cooling cells in row 406f by the micro-reactors 405 going left to right and back again to complete each PCR heating and cooling cycle (heat addition is by trace heat resistor elements under the surface, cooling is performed by Peltier or thermoelectric device, or by convective cooling from a fluid line under the chip). After an appropriate number of amplification cycles the micro-reactors 405 are allowed to advance along the chip 401. The micro-reactors 405 can be interrogated in row 406g in the optical detection zone 416.

Following amplification, the system does not need decontamination due to the isolation of the chemical reactants. In the next row 406h, empty or "dud" droplets are transported off the device (as determined by optical interrogation), while "hot" droplets continue along their rows. These droplets are then split for archival, with one half advancing off the chip up or down its column to an archival matrix 417 in row 406h. The other half of the droplet then proceeds for further processing such as capillary electrophoresis serving a specific row.

Specific Embodiment—System 500

Figure 5:
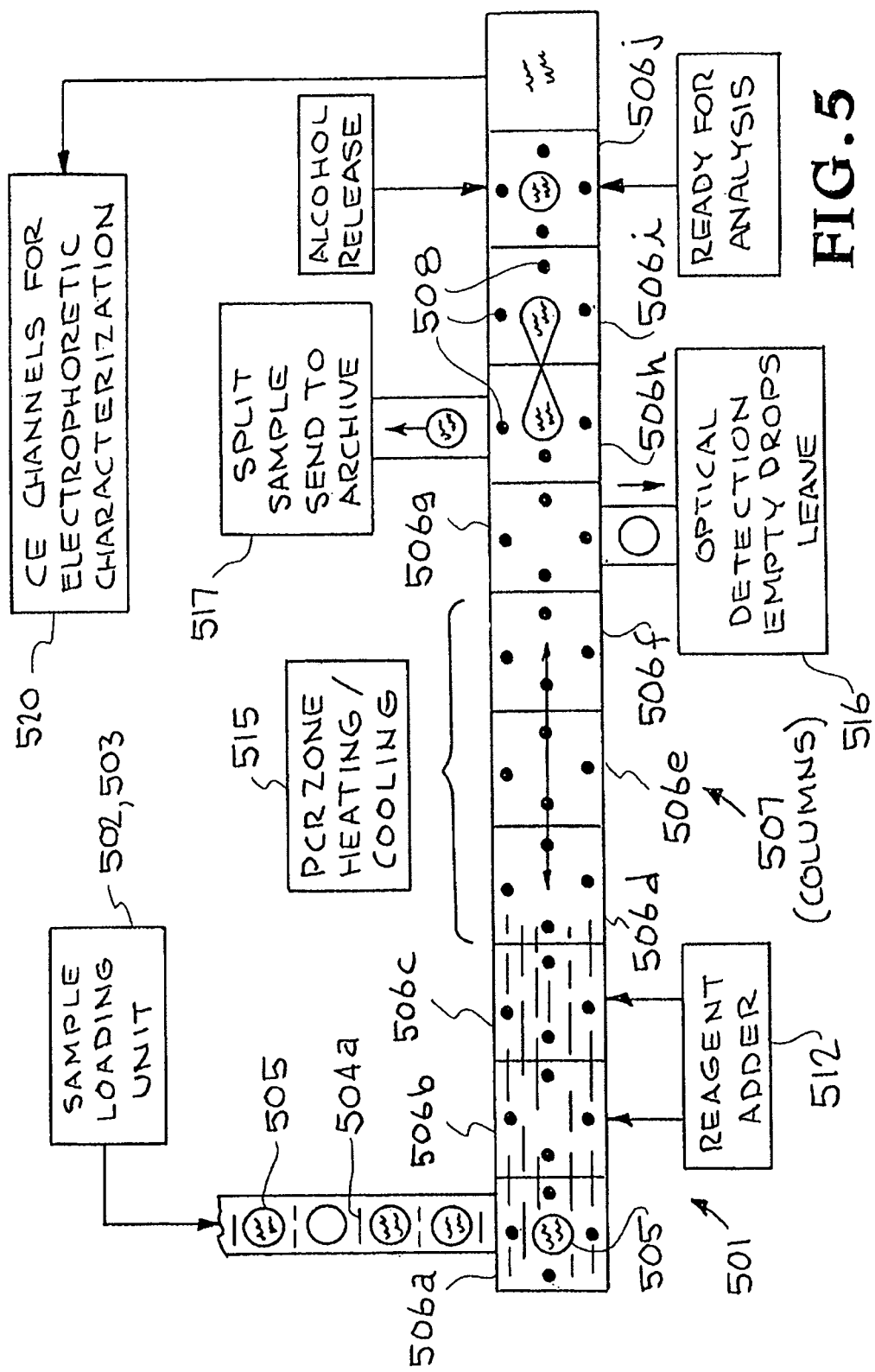
FIG. 5 illustrates an embodiment of a system that includes CE channels for electrophoretic characterization.

Referring now to FIG. 5, another embodiment of a system incorporating the present invention will be described that includes CE channels for electrophoretic characterization. The system is designated generally by the reference numeral 500. The system 500 contains the basic structural elements of the embodiments shown in FIGS. 1, 2, 3, and 4. The elements of the system 500 show in FIG. 5 used to describe the system 500 with CE channels for electrophoretic characterization 520 include a planar substrate 501, a sample loading unit 502 that can include a droplet generator, a sample 503 carried by a carrier fluid 504, droplets or micro-reactors 505, rows 506a-i, columns 507a-j, and electrodes 508.

The sample loading unit 502 introduces the micro-reactors 505 into row 506a. The micro-reactors 505 can be moved in columns 507 a-j using the electrodes 508 to provide a voltage differential that moves the micro-reactors 505 from one cell to another in columns 507 a-j. The reagents added section 512 in rows 506b-c allows the adding of reagents for further processing.

The droplets, each of which provide an isolated mobile PCR reactor 505 containing lysed-particle analyte plus reagent and buffer mixture, moves into PCR rows 506d-f of the PCR zone 515. The micro-reactors 505 are cycled from heating cells in row 506d to cooling cells in row 506f by the micro-reactors 505 going left to right and back again to complete each PCR heating and cooling cycle (heat addition is by trace heat resistor elements under the surface, cooling is performed by Peltier or thermoelectric device, or by convective cooling from a fluid line under the chip). After an appropriate number of amplification cycles the nucleic acids exceed the limits of detection of real time feedback from the optical interrogation system and fluorescent-labeled TaqMan type probes within the droplets, the droplet with amplified nucleic acids is then allowed to advance along the chip. Following amplification, the system does not need decontamination due to the isolation of the chemical reactants. In the next row

506g, empty or "dud" droplets are transported off the device (as determined by optical interrogation), while "hot" droplets continue along their rows. These droplets are then split for archival, with one half advancing off the chip up or down its column to an archival matrix 517 in row 506h. The other half of the droplet then proceed for further processing such as capillary electrophoresis serving a specific row. Selected droplets may then be assigned to one of the many available CE channels for electrophoretic characterization 520. Voltage actuation of channel electrodes alone, or in concert with laminar fluid flow over the chip forces the droplet into the CE channel.

In another embodiment, overlaid high pressure pads may combine with electrostatic potential to force the droplet into the CE channel for characterization. In another embodiment, the planar motion is performed by rastering optical tweezers across the planar substrate. In another embodiment, the planar motion is performed by energizing electromagnets distributed on the planar surface.

Specific Embodiment—System 600

Figure 6:
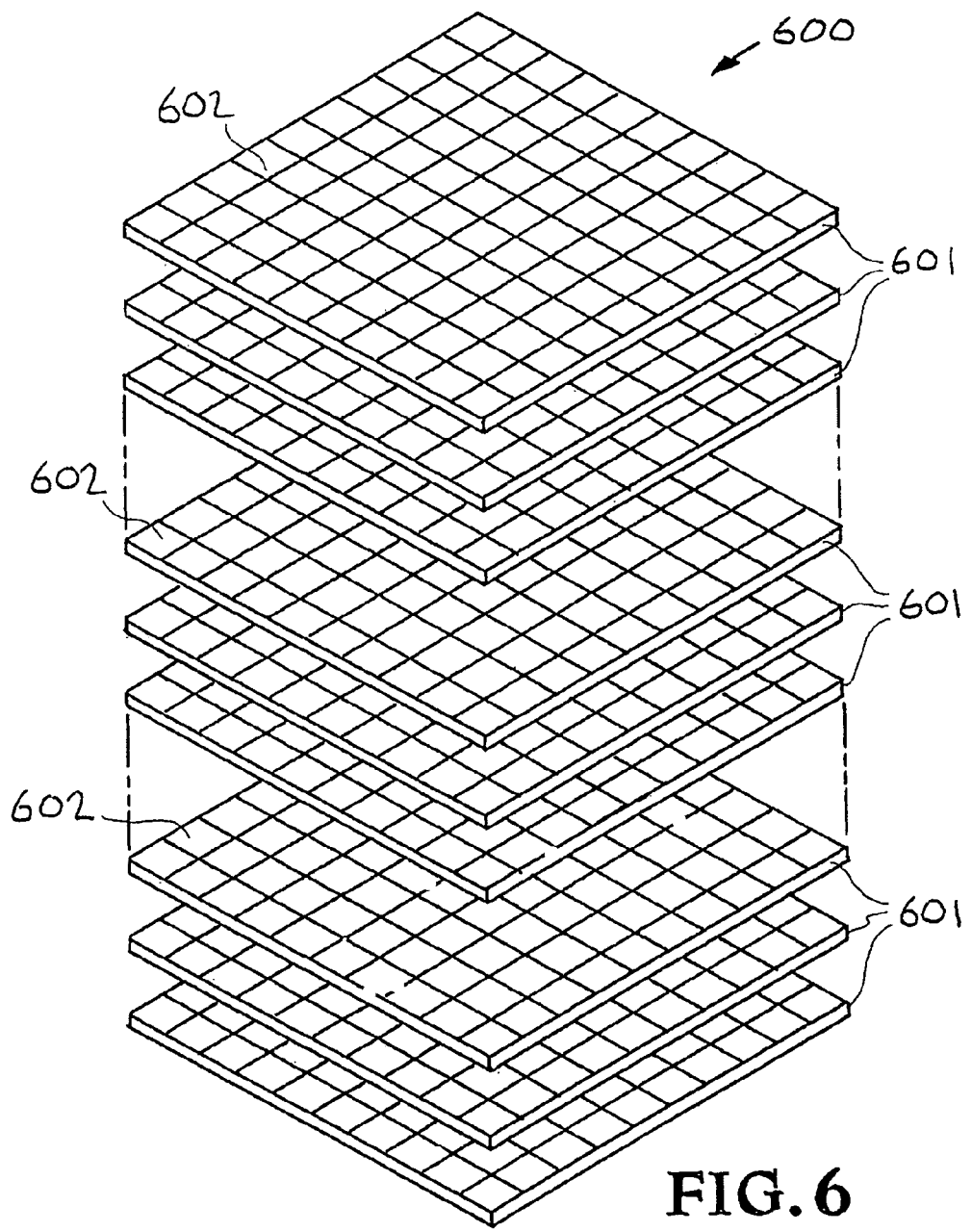
FIG. 6 illustrates another embodiment of a system incorporating the present invention.

Referring now to FIG. 6, another embodiment of a system incorporating the present invention will be described. The system is designated generally by the reference numeral 600. The system 600 is a multi tray system for chip-based sorting, amplification, detection, and identification of a sample. The system 600 includes multiple trays 601. Each of the multiple trays 601 contains multiple chip arrays 602. Each chip array 602 contains the basic structural elements of the embodiments shown in FIGS. 1, 2, 3, 4, and 5.

Chip-Based Sorting, Amplification, Detection, and Identification

The present invention, provides a sample analysis system capable of performing, singly or in combination, reagent and analyte mixing, cell, lysing, nucleic acid amplification, optical detection and discrimination, and nucleic acid detection and characterization.

Micro-Reactor Generator System (MGS)

The MGS system performs analyte mixing and injection, sample isolation, and system decontamination functions. Although multiple embodiments of the MGS system can be used for this invention, there are several key components, including: a hydrophobic carrier fluid, a fluid propulsion and metering device (typically a syringe pump), a fluidic channel with a T or cross junction, or a fixed orifice forcing the dispersion of the analyte and reagent aqueous solution into the hydrophobic carrier fluid, a multi-port selection valve for channel priming, and a variable width injector channel for controlling droplet spacing and velocity. The pump is used to draw and pump fluids through the flow circuit.

The hydrophobic carrier fluid provides the medium for translating the pump movements info fluid motion and for creating the spherical droplets that serve as the nanoscale reactors. This occurs due to the immiscibility of the hydrophilic droplets within the hydrophobic flow, as the sheared aqueous fluid relaxes into a spherical form to minimize surface tension (by minimizing surface area). Continuous flow of both, the hydrophobic carrier fluid and the aqueous reagent fluid ensures both the production and separation of the nanoscale reactors, eliminating the chance of cross-contamination. The performance characteristics of the pump allow for precise and accurate metering of the flow rates which determine droplet size under the relation:

$$D_h = \sigma Dh3/\mu Qi,\qquad \text{[Equation 1]}$$

where $D_h$ is the hydraulic radius of the channel at the junction, Qi is the volumetric flow rate in m3/s, σ is the surface tension in kg/s2, μ is the viscosity in kg/(m*s).

The device is a planar substrate consisting of a surface zone matrix of N rows by M columns. Discrete "digital" microreactors of an aqueous mixture can be moved around on the planar substrate to effect different chemical reactions and/or droplet transportation and processing, the substrate may also incorporate trace electrodes to heat the droplet micro-reactors to add thermal energy for desired chemical reactions such as PCR, polymerase chain reaction. Alternatively, the substrate may employ other methods such as optical or electromagnetic droplet heating to serve the same purpose. Droplet locomotion may be executed by dielectrophoresis (driven by an array of equi-spaced square electrodes on the planar surface), magnetophoresis (similar to dielectrophoresis but driven, by an array of surface electromagnets), optical trapping (driven by orthogonal laser beams that periodically raster scan the surface and move droplets from one cell or zone to an adjacent cell or zone by optical trapping or optical tweezers, or finally by optically-driven substrate surface charge localization.

Optical trapping is due to the dipole force of incident light on a dielectric abject, such as a water droplet. This dipole force results from the interaction between the electrical field of the incident light wave and the induced dipole that EM wave creates within the dielectric particle (droplet). This causes a gradient force on the particle described by:

$$F = \frac{1}{2} a \times \nabla E^2 \qquad \text{[Equation 2]}$$

where E is the electric field and a is the polarizability of the particle. When the incident light wavelength is less than the particle diameter, a Ray-Optics analysis is employed. A more complete description of the scattering and gradient forces by the laser beam is given by Prasad, Paris N., "Introduction to Biophotonics", John Wiley, NJ. The gradient force moves the particle to the waist of the incident beam and the scattering force must be balanced by one of gravity, buoyancy, or drag in a flow field.

The planar digital geometry of the proposed device allows for dividing the sample into multiple aliquots for subsequent analysis serially or in parallel with multiple streams, adding primers and reaction enzymes, chemicals to lyse cells or viral particles, etc. The scalability of the architecture allows for multiple different reactions to be tested against aliquots from the same sample, and for multiple droplets to be processed simultaneously. Decontamination by flushing the channels dilute solution of sodium hypochlorite, followed by deionized water can be used periodically to refresh the planar substrate.

One specific embodiment of this system is as follows. A complex environmental or clinical sample is prepared using known physical (ultracentrifugation, filtering, diffusion separation, electrophoresis, cytometry, etc.), chemical (pH), and biological (selective enzymatic degradation) techniques to extract and separate target nucleic acids or intact individual particles (e.g. virus particles) from background (i.e. intra- and extra-cellular RNA and DNA from host cells, pollen, dust, etc.). This sample, containing relatively purified nucleic acid or particles containing nucleic acids (e.g. viruses), could be split into multiple parallel channels and mixed on the planar substrate with appropriate reagents required for reverse transcription and subsequent PCR (primers, probes, dNTPs, enzymes). Each of these mixes are then introduced in such a way that statistically no more than a single RNA/DNA is present in any given microreactor. For example, a sample containing 106 target RNA/DNA would require millions of microreactors to ensure single RNA/DNA distribution.

Optical Detection and Cell Lysing

In one embodiment the device may employ optical detection of the aqueous droplets functioning as miniature reactors. The droplets may be irradiated by electromagnetic radiation such as that from a laser to create a shock wave inside the droplet sufficient to lyse the bacterial cell wall or protein capsids, releasing target nucleic acids (RNA and DNA) within the droplet reagents. Lysing could also be achieved using temperature by radiative heating such as that from a laser, or chemical enzymes that rupture the cell wall, or ultrasound-generating piezoelectric actuators that focus acoustic pressure on the cell walls, Lysing is necessary to make the nucleic acids accessible to the reagents used for amplification and or detection. Alternatively, samples could be lysed before they are introduced into the device, making this component optional. The advantage of performing in-situ lysis on the viruses or cells within the droplets is the ability to maintain, correlation between the Initial target organism and the analyzed genomic material. This is important if other parallel detection techniques (physical, proteomic) are added, (see Selective Encapsulation of Single Cells and Subcellular Organelles into Picoliter- and Femtoliter-Volume Droplets. Analytical Chemistry, Vol. #77).

Nucleic Acid Amplification

Initial concentration of targeted organisms will be unknown, and can vary over many orders of magnitude. For this reason many droplets will be generated that will contain no genetic material to amplify. The proposed sorting system will advantageously only select the droplets that have a sufficient quantity of post-amplified nucleic acid material to characterize. This is performed by the interrogation of each droplet by an orthogonal laser beam, to excite a fluorescent reporter that was supplied to each droplet in the reagent mix. This could be art intercalating dye that only fluoresces when bound to double stranded nucleic acids such as segments of PCR product. A detector senses the fluorescence if applicable and reports to the controller the presence of a "hot" droplet. This droplet, moving along its own row of adjacent zones on the planar substrate is then selected for characterization by capillary electrophoresis and/or archival. Other types of luminescence techniques could be used for optical droplet discrimination, including chemiluminescence or bioluminescence which do not require an external excitation source simplifying instrumentation design and have inherently low back-ground emission for highly sensitive detection. Addition, of this component greatly simplifies the design of the instrument, since it greatly reduces the number of parallel capillary electrophoresis or electrophoresis channels that are necessary to characterize the selected amplicons. In one embodiment droplets selected for electrophoresis will be sorted to the electrophoresis channel by optical trapping while the "empty" droplets move on to waste. In another embodiment, droplets selected, for electrophoresis will be sorted to the electrophoresis channel by dielectrophoresis migration down their rows toward the gel or capillary electrophoresis channels while the rest of the droplets are moved orthogonally up or down their columns to waste. In an alternative embodiment, the dielectrophoresis electrodes may be replaced with electromagnetics to propel and sort the particles.

In the publication, "Continuous Monitoring of Infectious Biological Agents", Analytical Chemistry v 75, pp 3446-3450 detection occurs much earlier using this method, since the total number of thermal cycles in significantly reduced by the concentration of amplicon is extremely small, volumes. The disadvantage of this method, however, is only a limited number of fluorescent colors can be reliably discriminated. Also, Taq-based primer/probes are generally selected to target very specific regions of the genome, so discovery of unknown viruses or microbes in impossible.

The present invention provides for nucleic acid characterization for novel or unknown viruses and bacteria by microcapillary, capillary, or gel electrophoresis due to the ability to interface with an electrophoresis system either on the device or connected to it. A preferred embodiment of the device maintains the presence of an array of selectable, independently programmable capillary electrophoresis (CE) lanes on the chip or orthogonal to it running perpendicular to parallel rows of advancing micro-reactors. As selected droplets enter into open CE channels, an electric potential fired on the CE electrodes causes migration of the droplet of Interest into the CE channel.

In one embodiment, the droplet can be captured by electrostatic attraction alone. In another embodiment with the capillaries perpendicular to the planar substrate, a combination of electrostatic attraction and mechanical actuation can be combined to capture individual droplets. (Mechanical actuation is controlled by overlaying pressurized gas lines in an orthogonal pattern above and parallel to the CE channels which, when pressurized, flex the cover layer of the device above the open channel, deflecting the hydrophobic cover toward the droplet, which is repulsed into the open port. In another embodiment a combination of electrostatic and magnetic force may be employed to move the droplets into the CE channels. In another embodiment, a combination of acoustic pressure from piezoelectric transducers and electrostatic attraction may be used to move the droplets into the channel. In another embodiment, a combination of optical pressure from an integrated optical trap may be used to with electrostatic force to move droplets into the channel.

The present invention provides for the droplet to be split if desired prior to CE channel entrance to allow for a fraction of the initial droplet to be carried off the row (up the column) to an archival aspiration port.

An applied potential field in the electrophoresis channels attracts the nucleic acid fragments and separates them according to their charge to size ratio due to the presence of an appropriate molecular sieve. The sieve acts to retard the nucleic acid flow. Because of this action the differing lengths of nucleic acids become separated into bands as they migrate with solvent ions along the electrophoresis channel. The present invention describes a system that will then image the CE channels to detect the fluorescence of tagged nucleic acid bands as they migrate down the channels. In a preferred, embodiment the system contains multiple CE channels in parallel with a charge coupled device (CCD) imaging system detecting the banding patterns.

To perform calibration of the electrophoresis channels a few of the droplets will be seeded with nucleic acid "Ladders", sequences of different lengths that vary by a constant number of bases. These "ladders" when amplified in PCR and run on some of the device's electrophoresis channels will ensure that the PCR reagent mixing, thermal heating, and electrophoretic separation, are functioning appropriately on the device. Furthermore, since multiple flow channels can be run in parallel, an entire flow channel can be employed to run only calibration and control nucleic acids. These controls will serve as "fiducials" to provide a banded image useful in diagnosing and confirming device performance.

Characterizing the products generated by the polymerase chain reaction can give information about the target genome that was amplified. The PCR reaction can be designed to generate specific products, or amplicons, with distinct sizes (i.e. lengths, number of bases), Electrophoresis can be used to separate PCR products according to size. It is important to have size reference standards that can be used for calibrating the electrophoresis process. DNA ladders or size reference standards can be incorporated into individual droplets and transported to the electrophoresis system. They could also be directly injected into the electrophoresis system.

A synthetic virus construct such as armored RNA can be used as an end-to-end system control and would very closely mimic the behavior of real virus or biological particle that could be present in the sample. It can be spiked to the sample or added in line. The control would provide information of sample addition, mixing, droplet formation, reagent addition, extraction, sample purity, sample preparation, particle lysing, reverse transcription, PCR amplification and detection. The control could have its own set of PCR primers and could be either co-exist in a droplet with the target or in its own droplet. The PCR primers for the control, can be designed to generate products that have distinct sizes that cover the range and resolution required to identify and characterize electropherograms from targets, essentially generating size ladders or reference standards in situ. The sequence target used for calibration can be made synthetically so that the products can be used as sequencing controls or other down stream characterization processes. The control can also yield information regarding any loss of specificity or sensitivity of the device.

In another embodiment, droplets can be barcoded and tracked as they are transported throughout each module of the system. Barcoding can be done with particles, such as beads, crystals, and identified using fluorescence, spectral signature or other unique signature identifiers. Barcodes can be made from unique combinations of particles, or an array of uniquely identifiable particles. Their size could be tailored (micrometers to nanometers) and the materials can be inert so as not to affect performance of the system or the assays. It droplets need to be manipulated, such as split one droplet into 2, the identify of the original droplet can be tracked and correlated with results from different (parallel) detection platforms.

While the invention may be susceptible to various modifications and alternative forms, specific embodiments have been shown by way of example in the drawings and have been described in detail, herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for chip-based sorting and detection of a sample, consisting of:
    a single planar substrate, said single planar substrate having a single planar surface that is divided into cells;
    said cells arranged on said single planar surface of said single planar substrate in multiple rows and multiple columns wherein said multiple rows are parallel and wherein said multiple columns are parallel and wherein said multiple rows and said multiple columns intersect;
    electrodes in said cells in said multiple rows and multiple columns on said single planar substrate;
    a carrier fluid in a carrier fluid source wherein said carrier fluid is directed onto said single planar surface of said single planar substrate and wherein said carrier fluid washes all of said single planar surface of said single planar substrate,
    a droplet generator connected to said carrier fluid source and said carrier fluid,
    a sample source containing the sample connected to said droplet generator;
    wherein said carrier fluid, said droplet generator, and the sample from said sample source produce micro-reactors containing the sample in said carrier fluid with said micro-reactors delivered onto said single planar surface of said single planar substrate;
    a microprocessor connected to said electrodes in said cells for manipulating said micro-reactors on said single planar surface of said single planar substrate and directing said micro-reactors containing the sample in said carrier fluid into said cells in said multiple rows and multiple columns on said single planar surface of said single planar substrate using said electrodes, and
    a detector positioned to interrogate the sample contained in said micro-reactors on said cells in said multiple rows and multiple columns on said single planar surface of said single planar substrate.

2. The apparatus for chip-based sorting-and detection of a sample of claim 1 wherein said multiple rows consists of at least ten rows and wherein said multiple columns consists of at least ten columns.

3. The apparatus for chip-based sorting-and detection of a sample of claim 1 wherein said multiple rows consists of ten rows and wherein said multiple columns consists of ten columns.

4. The apparatus for chip-based sorting and detection of a sample of claim 1 wherein said multiple rows consists of more than ten rows and wherein said multiple columns consists of more than ten columns.

5. The apparatus for chip-based sorting and detection of a sample of claim 1 wherein said multiple columns consists of a single column and wherein said micro-reactors are delivered into said single column and onto said single planar surface of said single planar substrate and into said multiple row and said multiple columns.

6. The apparatus for chip-based sorting and detection of a sample of claim 1 wherein said micro-reactors are delivered into said multiple columns and onto said single planar surface of said single planar substrate and into said multiple rows.

7. A method of chip-based sorting and detection of a sample, consisting of the steps of:
    providing a single planar substrate having a single planar surface;
    dividing said single planar surface of said single planar substrate into cells,
    arranging said cells on said single planar surface of said single planar substrate in multiple rows and multiple columns;
    positioning electrodes in said cells in said multiple rows and multiple columns on said single planar surface of said single planar substrate;
    providing a carrier fluid in a carrier fluid source and directing said carrier fluid onto said single planar surface of said single planar substrate so that said carrier fluid washes all of said single planar surface of said single planar substrate,
    providing a droplet generator connected to said carrier fluid source and said carrier fluid,
    providing the sample in a sample source that is connected to said droplet generator wherein said carrier fluid, said droplet generator, and the sample are adapted to produce microreactors containing the sample;
    using said droplet generator, said carrier fluid, said sample source, and the sample for producing said micro-reactors containing the sample and delivering said micro-reactors containing the sample to said cells in said multiple rows and multiple columns on said single planar surface of said single planar substrate;

connecting a microprocessor to said electrodes in said cells in said multiple rows and multiple columns on said single planar surface of said single planar substrate;

using said microprocessor for manipulating said micro-reactors in said cells in said multiple rows and multiple columns on said single planar surface of said single planar substrate, and using a detector to interrogate the sample contained in said micro-reactors in said cells in said multiple rows and multiple columns on said single planar surface of said single planar substrate.

8. The method of chip-based sorting and detection of a sample of claim 7 wherein said step of arranging said cells on said single planar surface of said single planar substrate in multiple rows and multiple columns consists of arranging said cells on said single planar surface of said single planar substrate in at least ten rows and at least ten columns.

9. The method of chip-based sorting and detection of a sample of claim 7 wherein said step of arranging said cells on said single planar surface of said single planar substrate in multiple rows and multiple columns consists of arranging said cells on said single planar surface of said single planar substrate in ten rows and ten columns.

10. The method of chip-based sorting and detection of a sample of claim 7 wherein said step of arranging said cells on said single planar surface of said single planar substrate in multiple rows and multiple columns consists of arranging said cells on said single planar surface of said single planar substrate in more than ten rows and more than ten columns.

* * * * *